(12) United States Patent
Culp

(10) Patent No.: US 7,118,374 B2
(45) Date of Patent: Oct. 10, 2006

(54) ENHANCED TOOTH SHADE GUIDE

(75) Inventor: Lee Culp, Bradenton, FL (US)

(73) Assignee: Ivoclar Vivadent AG, Schaan (LI)

( * ) Notice: Subject to any disclaimer, the term of this patent is extended or adjusted under 35 U.S.C. 154(b) by 317 days.

(21) Appl. No.: 10/456,586

(22) Filed: Jun. 9, 2003

(65) Prior Publication Data

US 2004/0248057 A1    Dec. 9, 2004

(51) Int. Cl.
A61C 19/10    (2006.01)
A61C 13/08    (2006.01)

(52) U.S. Cl. .................... 433/26; 433/203.1
(58) Field of Classification Search ............... 433/26, 433/203.1
See application file for complete search history.

(56) References Cited

U.S. PATENT DOCUMENTS

| | | | |
|---|---|---|---|
| 3,405,446 A | 10/1968 | Wiener | 32/1 |
| 3,861,044 A | 1/1975 | Swinson, Jr. | 32/17 |
| 3,975,760 A | 8/1976 | Yamanaka et al. | 358/41 |
| 3,986,777 A | 10/1976 | Roll | 356/176 |
| 4,016,598 A | 4/1977 | Yamanaka | 358/41 |
| 4,106,056 A | 8/1978 | Nagumo et al. | 358/50 |
| 4,110,826 A | 8/1978 | Möllgaard et al. | 364/526 |
| 4,247,202 A | 1/1981 | Failes | 356/310 |
| 4,414,635 A | 11/1983 | Gast et al. | 364/526 |
| 4,518,258 A | 5/1985 | Broersma | 356/405 |
| 4,547,074 A | 10/1985 | Hinoda et al. | 356/405 |
| 4,575,805 A | 3/1986 | Moermann et al. | 364/474 |
| 4,591,900 A | 5/1986 | Heeb et al. | 358/44 |
| 4,616,933 A | 10/1986 | Lévêque et al. | 356/416 |
| 4,623,973 A | 11/1986 | Hoffrichter et al. | 364/526 |
| 4,654,794 A | 3/1987 | O'Brien | 364/413 |
| 4,657,399 A | 4/1987 | Hall | 356/421 |
| 4,692,481 A | 9/1987 | Kelly | 523/219 |
| 4,802,850 A | 2/1989 | Boon | 433/26 |
| 4,813,000 A | 3/1989 | Wyman et al. | 364/526 |
| 4,836,674 A | 6/1989 | Lequime et al. | 356/319 |
| 4,881,811 A | 11/1989 | O'Brien | 356/323 |
| 4,903,122 A | 2/1990 | Ozaki et al. | 358/48 |
| 4,919,617 A | 4/1990 | Antons et al. | 433/26 |
| 4,978,296 A | 12/1990 | Antons et al. | 433/26 |
| 5,012,431 A | 4/1991 | Stanziola | 364/526 |
| 5,055,040 A | 10/1991 | Clar | 433/26 |
| 5,124,797 A | 6/1992 | Williams et al. | 358/225 |
| 5,149,267 A | 9/1992 | Longhini et al. | 433/26 |
| 5,177,694 A | 1/1993 | Graham et al. | 364/526 |
| 5,231,472 A | 7/1993 | Marcus et al. | 356/402 |
| 5,240,414 A | 8/1993 | Thompson | 433/26 |
| 5,261,815 A | 11/1993 | Pozzi | 433/26 |
| 5,273,429 A | 12/1993 | Rekow et al. | 433/215 |
| 5,282,025 A | 1/1994 | Sato | 358/44 |
| 5,313,267 A | 5/1994 | MacFarlane et al. | 356/405 |
| 5,340,309 A | 8/1994 | Robertson | 433/69 |
| 5,373,364 A | 12/1994 | Krzyminski | 356/405 |
| 5,383,020 A | 1/1995 | Vieillefosse | 356/326 |
| 5,430,811 A | 7/1995 | Fukushima et al. | 382/254 |
| 5,431,562 A | 7/1995 | Andreiko et al. | 433/24 |
| 5,452,219 A | 9/1995 | Dehoff et al. | 364/474.05 |
| 5,498,157 A | 3/1996 | Hall | 433/26 |
| 5,529,492 A | 6/1996 | Yarovesky et al. | 433/26 |
| 5,549,476 A | 8/1996 | Stern | 433/223 |
| 5,587,912 A | 12/1996 | Andersson et al. | 364/468.04 |
| 5,659,625 A | 8/1997 | Marquardt | 382/118 |
| 5,685,712 A | 11/1997 | Fischer | 433/26 |
| 5,692,900 A | 12/1997 | Fischer | 433/26 |
| 5,733,126 A | 3/1998 | Andersson et al. | 433/223 |
| 5,766,006 A | 6/1998 | Murljacic | 433/26 |
| 5,851,115 A | 12/1998 | Carlsson et al. | 433/215 |
| 5,867,588 A | 2/1999 | Marquardt | 382/118 |
| 5,961,324 A | 10/1999 | Lehmann | 433/26 |
| 6,030,209 A * | 2/2000 | Panzera et al. | 433/26 |
| 6,038,024 A | 3/2000 | Berner | 356/326 |
| 6,093,019 A | 7/2000 | Morandi et al. | 433/29 |
| 6,132,210 A | 10/2000 | Lehmann | 433/26 |
| 6,206,691 B1 | 3/2001 | Lehmann et al. | 433/26 |
| 6,210,159 B1 | 4/2001 | Lehmann et al. | 433/26 |
| 6,328,563 B1 * | 12/2001 | Hobo | 433/26 |
| 2003/0190578 A1 * | 10/2003 | Lehmann | 433/26 |
| 2003/0235799 A1 * | 12/2003 | Cruz | 433/26 |

FOREIGN PATENT DOCUMENTS

| | | |
|---|---|---|
| EP | 0 360 657 A1 | 3/1990 |
| JP | 04301530 A | 10/1992 |
| WO | WO 86/03292 | 6/1986 |
| WO | WO 91/02955 | 3/1991 |
| WO | WO 95/15731 | 6/1995 |

* cited by examiner

*Primary Examiner*—Cary E. O'Connor
(74) *Attorney, Agent, or Firm*—Nixon Peabody LLP

(57) ABSTRACT

The invention relates to an enhanced electronic shade guide that includes addtitional hue-chroma information between the shades of existing shade guides and value information for the measured tooth. The shade guide provides a recipe for constructing a restoration or replacement for the tooth. A comparison of the patient's tooth to the stored tooth shades is preferably performed electronically by a suitable software program that contains the shade guide information of the present invention.

18 Claims, No Drawings

ENHANCED TOOTH SHADE GUIDE

FIELD OF INVENTION

The invention relates to electronic shade guides and methods for determining tooth shades. More specifically, the invention relates to an enhanced shade guide that includes a plurality of shades to accurately match the shade of a patient's tooth.

BACKGROUND OF THE INVENTION

A necessary step in altering a patient's tooth color is to determine the "shade" of the existing tooth. For example, those persons seeking a whiter, brighter smile are still assessed to establish their existing tooth color so that an appropriate before and after comparison can be made. Shade determination is even more important for those persons seeking reconstructive work, since one goal of the reconstructive process is to achieve a natural appearance. Therefore, it is important to know the existing tooth shade so that it can be accurately matched with the new restoration.

The dental profession has typically utilized standardized shade guides created by those companies which manufacture the reconstructive materials. One well-known shade guide is the Vita™ shade guide, which includes sixteen different shades. Other, less popular shade guides include those guides provided by Bioform™ and SR-Vivaden™.

These shade guides are utilized in a rudimentary fashion. The guide itself is a plastic plate with a plurality of removable color tabs that are shaped like a tooth, e.g., the front tooth. Typically, to assess a patient's tooth shade, a dentist removes one of the colored tabs and holds it up to the patient's tooth so that she can "eyeball" the closest match possible. Understandably, there are many variables to this method, some of which stem from the subjectivity of the dentist making the eyeball assessment.

To further complicate matters, the standard Vita™ Classic shade guide contains only sixteen shades ranging from A1 to D4. Needless to say, many patients' teeth do not match any of the sixteen shades. In that case, if the eyeball assessment is used, the dentist may attempt to combine two or more shades. Alternatively, if a computer or electronic shade analyzing system is being used, the analysis may result in a determination that the shade is almost exactly in between two shades. For example, a tooth may be 49% A4 and 51% B1 according to the analysis. In that case, the system will typically report the shade as B1, since that is the closest match.

Once the tooth shade is determined, the information is used relative to the particular procedure needed. In bonding or filling a tooth, for example, the composite materials required for the restoration are specified within the range of the shade guide, e.g., one of sixteen shades for the Vita™ range. More particularly, if a crown, bridge, or denture is needed, the patient's shade must be determined and communicated correctly to the lab that make the crown, bridge, or denture.

The process for selecting the porcelain for a particular tooth shade illustrates the difficulty in assessing and manufacturing the correct color match. If, for example, a crown of Vita™ shade A3 is desired, porcelain is built by hand with a paint brush onto a model of the tooth to be restored. The porcelain is built in layers on the model to achieve translucency and natural appearance. Each layer has a particular color and intensity associated with it. To generate shade A3, the technician follows a "recipe" that is given by the manufacturer Vident™, requiring a different shade for each layer of porcelain applied. If a doctor asks for a shade that is not a Vita™ standard shade, the technician typically seeks to achieve that shade by combining different porcelain shade combinations together, to increase or decrease the chroma, hue, and value of the shade.

Patients may also desire to change the shade of their teeth, generally by whitening or otherwise brightening them. A necessary first step in this regard is to determine the shade of the existing teeth. The goal may be to whiten all of the teeth to a certain predetermined shade, or it may be to match the shades of some of the teeth to the others. Currently, the dental professional will utilize a standardized shade guide, such as VITA™, BIOFORM™, and CHROMASCOP™. There is a great deal of subjectivity involved in such a measurement and the dental professional may not be sufficiently skilled or qualified for the task. The lighting and ambient light in the room can also affect selection of the tooth shade.

Thus, there is a need for a shade guide system for obtaining accurate color information from a patient wherein reliable, reproducible information is obtained regarding the shade of the patient's tooth. The shade guides known in the art are too limited to provide enough options to accurately match a patient's tooth color. The present invention provides these and other features in a manner which is not heretofore known in the art.

SUMMARY OF THE INVENTION

The present invention relates to an enhanced shade guide, which preferably is electronic, for determining tooth color that includes a plurality of shades which includes hues, chroma, and value information. The shades correspond to porcelain recipes for constructing a replacement tooth, crown, bridge, or denture. The shades include the conventional shades and subdivisions between the conventional shades. The value information includes white, gray, and black subdivisions between. In one embodiment, the subdivisions include 4 to 14 divisions between the conventional shades, in another embodiment, 3 to 13 divisions. The hue, chroma, and value information may be represented as a matrix.

The invention further relates to methods for determining a tooth color by generating an electronic image of a patient's tooth, storing the shade guide information, and comparing the color information of the image with the stored shade guide information. A computer readable medium may be provided containing programs for performing this method.

The invention also includes a system for determining a patient's tooth color that includes a camera and a shade analyzer that includes a color processor, a storage medium for storing a shade guide, a color correlator for comparing the patient's tooth information to the information of the shade guide, and means for communicating the identified to shades to the user.

DETAILED DESCRIPTION OF THE INVENTION

In the present invention, the term "color" is used to refer to the overall appearance of an object, such as a patient's tooth, or to portions of the object. The invention enables a dentist or technician to determine specific shades for the overall visual impression of the tooth or for any segment or portion of the tooth. When the tooth to be replaced is in the rear portion of the mouth or in other, less visible areas, the entire replacement tooth can be simply made of a single color. In contrast, if the tooth is in the front of the patient's mouth or is more prominently visible, portions of the replacement tooth can be made of different tooth shade colors to match as closely as possible the different colors of the original tooth. The different portions can be parts of the tooth, e.g., the cervical, incisal, and central regions, or can be based on different discrete portions of the tooth that have different colors.

The invention relates to an electronic shade guide and a method for determining a patient's tooth shade. Tooth shades are generally measured for three basic characteristics-hue, chroma, and value. Hue refers to whether the color appears red, yellow, blue, etc. Chroma refers to the intensity of the color. The value of a color refers to the amount of white or black in a color, its lightness or darkness.

The basic VITA™ shade guide contains four shade families referring to four shade hues. A shades have a red-brown character, B shades have a red-yellow character, C shades have a gray character, and D shades have a red-gray character. The chroma is shown by the number following the letter. Thus, the 16 shade guides in the basic VITA™ shade guide include: A1, A2, A3, A3.5, A4, B1, B2, B3, B4, C1, C2, C3, C4, D2, D3, and D4. The value is only accounted for by the fact that C and D have lower values than A and B.

The present invention greatly expands the color properties of this known shade guide. There are numerous shades that fall in between the conventional shades of the known shade guide. Each new shade corresponds to a recipe to more exactly match porcelain for reconstructive use. The recipe will contain a more precise hue-chroma and a new entry for value or brightness of the shade.

The hue-chroma part of the recipe includes intermediate hue-chromas between the hue-chroman in the existing VITA™ shade guide. For example, instead of only A1 and A2, the present invention accounts for A1.1, A1.2, A1.3, . . . , A2. For A1.1, the corresponding recipe would include 1 part of A2 with 9 parts of A1. For A1.2, 2 parts of A2 with 8 parts of A1, and so on. In this way, the hue-chroma is significantly more precise than that of the VITA™ shade guide.

The second part of the shade includes information on the value of the shade. This part would provide the recipe for the amount of white, black, or gray that would be added to the color. For example, A3.5(+2) would include 2 parts of white added to A3.5 and A3.5(−2) would include 2 parts of black added to A3.5.

The new shade guide may be easily represented as a matrix, with the hue-chroma information along the horizontal axis and the value information on the vertical axis. In one embodiment, the matrix may be represented as follows:

In this way, in this embodiment, the shade guide of the present invention accounts for nine shades between each shade in the VITA™ shade guide, as well as up to five values above and up to five values below the standard shade guide with the brightest value being white and the darkest value being black. There may be about four to fourteen and preferably ten subdivisions between the conventional shade guide. Fewer than four subdivisions would not give the desired precision of the invention, and more than fourteen subdivisions would be within the scope of the invention, but would be practically difficult. Although greater numbers of divisions are not outside of the invention, more than fourteen divisions would generally not result in shades with significant visual differences, as long as at least four to fourteen divisions are provided.

The particular location on the matrix provides a particular recipe for constructing a porcelain shade combination for constructing an accurate tooth replacement, such as a crown, bridge, or denture that matches the original tooth color or the color of the surrounding teeth much more precisely than that of the prior art. For example, a complete recipe might be: C1.2(−4). This would indicate to a technician that the porcelain recipe should include 8 parts of C1, 2 parts of C2, and 4 parts of black.

Of course, a patient's tooth can have multiple colors so that the shade guide can provide color matches for different portions of the tooth. As noted above, this can be achieved by defining surface areas or portions of the tooth that have the same or a similar color, and then providing a color match for those areas or portions. By this method, the entire tooth can be mapped into areas of different color so that the replacement tooth is a visually identical match to the current tooth. The color correlator is more accurate than a human eye, but this level of precisions is not required. The dentist or technician can refine the color map to facilitate construction of the replacement tooth in a way that is economically feasible without compromising the final appearance of the replacement tooth. Since the present invention provides much finer color differences in its shade colors than was previously known in the art, the resulting replacement tooth is a much closer color match to the original tooth than was previously possible.

The enhanced shade guide of the present invention may also be used to assist a dental professional in whitening or brightening a patient's teeth. The patient can choose a particular shade that they desire. The dental professional can calculate the difference between the desired tooth shade and the patient's actual tooth shade to determine the recipe for the necessary amount of whitening material to achieve the desired shade.

| (+5) | . | . | . | . | . | . | . | . | . | . |
|---|---|---|---|---|---|---|---|---|---|---|
| . | | | | | | | | | | |
| . | | | | | | | | | | |
| . | | | | | | | | | | |
| (+1) | | | | | | | | | | |
| A1, A1.1, A1.2, . . . , B1, B1.1, . . . , C1, C1.1, . . . , D2, D2.1, . . . , D3.9, D4 | | | | | | | | | | |
| (−1) | | | | | | | | | | |
| . | | | | | | | | | | |
| . | | | | | | | | | | |
| . | | | | | | | | | | |
| (−5) | . | . | . | . | . | . | . | . | . | . |

Although the invention may be used by eyeballing the tooth and comparing the shade to the standard shade guide of the present invention, preferably the shade matching is performed electronically with a camera and shade analyzer system. Any such system that can be loaded with software that contains a program that determines the tooth shade based on the present invention. For example, the systems disclosed in U.S. Pat. Nos. 5,766,006, 5,961,324, 6,132,210, 6,206,691, and 6,210,159 could be used with the present invention. The content of each of these patents is hereby incorporated by express reference thereto.

A number of different aspects of the invention are disclosed. In one aspect, the invention provides a system for determining the tooth shade of a patient's tooth. A camera, preferably an intraoral camera, captures the image of the patient's tooth, including color information representative of the tooth's color. A shade analyzer sub-system is in electrical communication with the intraoral camera, and preferably has (i) a color processing section for determining the color of the patient's tooth from the color information of the image; (ii) storage memory for storing a shade guide comprising a plurality of tooth shades which include hue, chroma, and value information, (iii) a color correlation section for comparing the color of the patient's tooth to the hue, chroma, and value information of the shade guide to identify a tooth shade with a color corresponding to the color of the patient's tooth, and (iv) means such as a display terminal for communicating the identified tooth shade to a user of the system.

In another aspect, the system includes a monitor used to display the color image to a user of the system. The shade analyzer sub-system thus communicates a tooth color representative of the identified tooth shade to the monitor, thereby providing a user of the system with a visual comparison of the patient's tooth color with the color of the identified tooth shade.

A camera, such as an intraoral camera, captures an image of the patient's tooth, including color information representative of the tooth's color. A shade analyzer system is in electrical contact with the camera, such that the shade information is transferred from the camera to the analyzer system. The analyzer system will generally include a color processor for determining the tooth color based on color information from the camera and a color correlation section for evaluating the color and identifying a tooth shade stored in memory that most closely matches the patient's tooth color.

A computer readable medium, such as a diskette, CD-ROM, DVD-ROM, smart card, or others known in the art, contains procedure codes for processing the data of the tooth obtained by a camera or similar intraoral device. The medium includes one or more programs that includes the shade guide information of the present invention, and procedure codes for comparing the data from the image of the tooth with the shade guide information to determine the closest match. Such media, as well as a hard drive or other type of computer storage equipment, may also be used as memory/storage devices in accordance with the present invention.

The color processor relays the recipe for the restoration to a lab technician, where the tooth shade may be matched to the shade of the tooth to be replaced, or to the patient's adjacent or contra-lateral teeth. When stored on a tangible medium, such as a computer diskette, the dental professional can simply forward the diskette to the laboratory for use by the technician. When the data are stored electronically on a computer, electronic files can be forwarded to the technician by e-mail. Using this information, the lab technician may construct a veneer of porcelain or other material, or can determine the proper shade to color the teeth. Each comparison can be electronic by software analysis or by visual comparison if the need arises, e.g., loss of electricity.

Advantageously, the shade guide information and recipe may also be stored in an electronic storage medium, such as a CD, a DVD, a computer hard drive, an electronic diskette, digital tape, a mini disc, flash card, smart card, or any of a number of other such storage media. Preferably, the image would be directly stored to a CD or DVD. The image can be directly stored on a card or other electronic storage medium in the camera, and then transferred to a computer hard drive, CD, or DVD after then images are obtained. In this way, the image may be conveniently saved with the patient's file and viewed at a later time, such as at a subsequent examination or for analysis by the dentist or referral specialist at a later time when the patient may be unavailable. The patient could also view the saved image to see a "before and after" effect for dental procedures, as well as to see what their teeth might look like if certain procedures were performed. This latter can be accomplished using an overlay of a dental standard coupled with the patient's scan. Suitable computer software can be used to merge the images, if desired.

Another but less preferred way of obtaining color information from the patient's tooth would be to include a plurality of reference colors adjacent to the tooth of interest when the images are being obtained. The resulting image can be processed with a color analyzer by the method disclosed in U.S. Pat. No. 5,177,694. The data stored in the color for making this comparison would be the shades of the present invention so that a more accurate color representation of the tooth can be made.

The invention also includes a method for determining the tooth shade of a patient's tooth, including the steps of: generating an electronic image of the patient's tooth with a camera, the image including color information representative of tooth color; determining the color of the patient's tooth from the color information of the image; comparing the color of the patient's tooth with the stored hue, chroma, and value information of the shade guide to identify one or more tooth shades having colors that correspond to those of the patient's tooth, the shade guide being stored in an electronic medium; identifying a tooth shade from the enhanced shade guide with a color corresponding to the color of a patient's tooth; and communicating the identified tooth shades to a user of the system.

A further method of the invention compares to tooth shade of a patient's tooth after the patient's teeth are cosmetically whitened, including the steps of: capturing a first image of the patient's tooth with an intraoral camera before the tooth is cosmetically whitened, the first image including first color information representative of a color of the tooth; processing the color information of the image to determine the color of the patient's tooth; comparing the color of the patient's tooth to a plurality of tooth shades corresponding to the enhanced shade guide, the tooth shades being stored in an electronic medium; identifying a tooth shade from the enhanced shade guide with a color corresponding to the color of the patient's tooth; whitening the teeth; communicating the identified tooth shade to a user of the system; and viewing the patient's tooth on a monitor after the whitening step while simultaneously displaying an image of the patient's pre-whitened tooth, to provide before and after imagery.

In another aspect of the invention, a process is provided for manufacturing a reconstructive tooth for a patient, including the step of: capturing the image of the patient's tooth with an intraoral camera, the image including color information representative of a color of the tooth; processing the color information of the image to determine the color of the patient's tooth; comparing the color of the patient's tooth to a plurality of tooth shades, the tooth shades being stored in an electronic medium; specifying one or more tooth shades, and any fractions thereof, having a combined color corresponding to the color of the patient's tooth; and painting one or more layers of porcelain onto a model of the patient's tooth, each of the layers of porcelain corresponding to the specified tooth shades and the fractions thereof.

The invention also includes a system for determining the tooth shade of a patient's tooth by utilizing color CCD cameras. In one aspect, a color CCD camera captures the image of the patient's tooth, including color information representative of a color of the tooth. A shade analyzer sub-system is connected for electrical communication with the CCD camera, and has (i) a color processing section for determining the color of the patient's tooth from the color information of the image, (ii) a storage section for storing shade information representative the enhanced shade guide of the present invention containing chroma, hue, and value information, (iii) a color correlation section for comparing the color of the patient's tooth to the shade guide to identify a tooth shade with a color corresponding to the color of the patient's tooth, and (iv) a section for communicating the identified tooth shade to a user of the system.

The system may include user interface equipment that permits the operator to interact with the shade analyzing system. User interface may include a keyboard, a mouse, a voice recognition system, and the like. The system may also include a monitor or of display device.

Communications equipment may be used with the system that permits inter-computer communications, for example, for the transfer of shade information between computers. Communications equipment may include a modem, an ethernet card, a digital subscriber line interface, a cable modem, etc. Other types of communications equipment are known to those skilled in the art.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A method for determining a patient's tooth color, which comprises:
    generating an electronic image of a patient's tooth wherein the image includes color information representative of the patient's tooth color;
    storing a shade guide comprising a plurality of shades which include hue, chroma, and value information, wherein the hue, chroma, and value information are presented in a matrix where hue and chroma are on one axis and value is on another axis; and
    comparing the color information of the image with the stored hue, chroma, and value information of the shade guide to identify one or more tooth shades having colors that correspond to those of portions of the patient's tooth.

2. The method of claim 1, wherein the shades comprise conventional tooth shades and subdivisions therebetween.

3. The method of claim 2, wherein the shades comprise about 4 to 14 subdivisions between the conventional shades.

4. The method of claim 1, wherein the value information includes white, black and gray subdivisions.

5. The method of claim 4, wherein the value information comprises about 3 to 13 subdivisions between white and black.

6. A computer readable medium containing one or more programs for performing the method of claim 1.

7. A shade guide for determining tooth color comprising a plurality of shades which include hue, chroma, and value information, wherein the hue, chroma, and value information are presented in a matrix where hue and chroma are on one axis and value is on another axis.

8. The shade guide of claim 7, wherein each shade corresponds to a porcelain recipe for constructing a replacement tooth, crown, bridge, or denture.

9. The shade guide of claim 7, wherein the shades comprise conventional shades and subdivisions therebetween.

10. The shade guide of claim 9, wherein the shades comprise about 4 to 14 subdivisions between the conventional shades.

11. The shade guide of claim 7, wherein the value information includes white, black, and gray and subdivisions therebetween.

12. The shade guide of claim 11, wherein the value information comprises about 3 to 13 subdivisions between white and black.

13. The shade guide of claim 7 in electronic form.

14. A system for determining a patient's tooth color, comprising:
    a camera having a lens for capturing an image of a patient's tooth, the image including color information representative of the patient's tooth color, and
    a shade analyzer sub-system connected for electrical communication with the camera, the shade analyzer having:
        (i) a color processor for determining the patient's tooth color from the color information of the image,
        (ii) a storage medium for storing a shade guide comprising a plurality of tooth shades which include hue, chroma, and value information, wherein the hue, chroma, and value information are presented in a matrix where hue and chroma are on one axis and value is on another axis,
        (iii) a color correlator for comparing the color of the patient's tooth to the hue, chroma, and value information of the shade guide to identify one or more tooth shades having colors corresponding to the patient's tooth color, and
        (iv) means for communicating the identified tooth shades to a user of the system.

15. The system of claim 14, wherein the shades comprise conventional shades and subdivisions therebetween.

16. The system of claim 15, wherein the shades comprise about 4 to 14 subdivisions between the conventional shades.

17. The system of claim 14, wherein the value information includes white, black, and gray subdivisions.

18. The system of claim 17, wherein the value information comprises about 3 to 13 subdivisions between the white and black.

* * * * *